United States Patent
Naumann

(10) Patent No.: US 7,897,111 B2
(45) Date of Patent: Mar. 1, 2011

(54) PIPETTING DEVICE

(75) Inventor: Uwe Naumann, Jena (DE)

(73) Assignee: Cybio AG, Jena (DE)

( * ) Notice: Subject to any disclaimer, the term of this patent is extended or adjusted under 35 U.S.C. 154(b) by 17 days.

(21) Appl. No.: 12/577,877

(22) Filed: Oct. 13, 2009

(65) Prior Publication Data

US 2010/0092342 A1 Apr. 15, 2010

(30) Foreign Application Priority Data

Oct. 14, 2008 (DE) .................. 20 2008 013 533 U

(51) Int. Cl.
*G01F 19/00* (2006.01)
*G01F 25/00* (2006.01)
(52) U.S. Cl. .................. 422/100; 73/1.74; 73/864.24; 73/864.25; 436/54
(58) Field of Classification Search .................. None
See application file for complete search history.

(56) References Cited

U.S. PATENT DOCUMENTS

| 3,963,148 | A | * | 6/1976 | Proni et al. .................. 222/132 |
| 5,365,798 | A | * | 11/1994 | Kressirer .................. 73/864.11 |
| 6,669,432 | B2 | * | 12/2003 | Hamel et al. ............ 414/331.05 |
| 6,982,063 | B2 | * | 1/2006 | Hamel et al. .................. 422/100 |
| 2003/0133838 | A1 | * | 7/2003 | Eichenlaub et al. ............ 422/58 |

FOREIGN PATENT DOCUMENTS

| AT | 314 850 | | 4/1974 |
| DE | 201 14 052 | U1 | 1/2002 |
| DE | 200 23 039 | U1 | 11/2002 |
| DE | 20 2007 013 040 | U1 | 12/2007 |
| EP | 0 569 851 | A1 | 11/1993 |
| EP | 1 612 561 | A1 | 1/2006 |
| WO | WO 02/096562 | A1 | 12/2002 |

* cited by examiner

*Primary Examiner*—In Suk Bullock
*Assistant Examiner*—Jennifer Wecker
(74) *Attorney, Agent, or Firm*—Duane Morris LLP

(57) ABSTRACT

A pipetting device, having a base plate, an elastic sealing plate that covers the outside of the base plate, and a plurality of pipetting channels arranged in a predetermined grid extending through the base plate and the sealing plate. A magazine is loaded in the same grid with the pipette tips, each pipette tip having a shoulder. The magazine is arranged in a magazine holder indirectly frictionally connected via the shoulders and the sealing plate with the base plate, and a drive motor, indirectly connected to the eccentric shafts of two identical eccentric drives that are permanently mounted on the support on the base plate. Each drive has an eccentric pin that is offset by a distance with respect to the axis of the eccentric shaft, and one T-shaped gravitational pendulum is suspended from each of the eccentric pins. The magazine holder is formed by a U-shaped magazine frame with a bearing surface on the inside. The magazine frame, on its lateral legs, is connected to the cross member of each gravitational pendulum so as to be able to lift and lower the magazine frame relative to the base plate.

5 Claims, 4 Drawing Sheets

PIPETTING DEVICE

FIELD OF THE INVENTION

The present invention relates to a pipetting device with a magazine grip as it is generically known from WO 02/096562.

BACKGROUND OF THE INVENTION

Generally speaking, a pipetting device which comprises one or more air-displacing piston stroke pipettes for use in laboratories serves to aspirate liquids from one container and dispense them into another container. The aspiration and/or dispensation of liquids can also take place in steps from or into different containers and with different liquids.

If liquids are frequently changed, it is useful if pipette tips that come into contact with the liquid to be transferred are designed so as to be replaceable and inexpensive, thus ensuring that carryovers and time-consuming rinsing steps during the liquid change are avoided.

As a rule, pipette tips are therefore injection-molded from a plastic material. The plastic materials used must be ultrapure, i.e., they should contain as few additives or plasticizers as possible to ensure that the transferred liquid is not contaminated, they should resist corrosion by chemicals and solvents commonly used in the laboratory, and they should be inexpensive.

It was found that a suitable plastic material for this purpose is polypropylene.

Pipetting devices were initially manufactured with only one channel and a manual drive. In this case, a pump system that is connected to the exchangeable pipette tip via an air channel (pipetting channel) is positioned inside the pipette.

The volume to be aspirated or dispensed is predetermined by the pump system and transferred to the liquid in the pipette tip via the air in the pipetting channel. In addition to the pump system, the quantity of air in the pipetting channel, the surface of the liquid level in the pipette tip and the cleanliness of the inlet and outlet aperture of the pipette tip, it is especially the hermetic seal between the pipetting channel and the pipette tip that plays an important role in ensuring the precision of the volume of aspirated or dispensed liquid.

This hermetic seal is typically implemented by creating a seal in the form of a cone between the pipette tip and the pipetting channel. In some systems, this seal is enhanced by an O-ring on the pipette cone. For manually operated pipettes, this principle offers the advantage that the pipette tip can be sealed off from the pipetting channel simply by sliding the pipette cone onto the pipetting channel cone. The tip can subsequently be just as easily released by using an ejector.

In addition to the single-channel pipetting device, multi-channel pipetting devices with a tandem arrangement of up to 16 pipetting channels have been developed.

In addition, pipetting devices with pipetting channels in two-dimensional configurations (8×12 and 16×24) have been designed, with the number and configuration of the pipetting channels being determined by the sample carriers that meanwhile had become widely accepted in practice, such as, inter alia, microtiter plates.

As the number of pipette tips that are to be simultaneously slid on and ejected increases, the cone principle described leads to an increasingly high degree of technical complexity.

Because of the given tolerances of the pipette tips in the area to be sealed, it is increasingly more difficult, as the number of pipetting channels increases, to hermetically mount all pipette tips. The manufacturing tolerances of the pipette tips must subsequently be compensated for by way of the elasticity of the pipette tips or by sealing means, such as O-rings on the cones, which is difficult because of the forces required, in particular in the case of 96- and 384-channel pipetting devices.

For this reason, a special sealing principle has been introduced for use with multi-channel pipetting devices, according to which the pipette tips are pushed with their front end against an elastic sealing plate that lies close to a flexurally stiff flat plate of the pipetting device into which the pipetting channels extend. The pipette tips are released simply by canceling the pressure. Effectively designing the front end of the pipette tips with an appropriately matched sealing surface of the sealing plate will make it possible readily to seal as many as 384 pipette tips at the same time as long as the sealing surface if protected against surface damage and contaminations.

However, this sealing principle again requires high contact pressure to ensure a simultaneous and effective seal for all pipette tips.

To introduce this contact pressure uniformly into all pipette tips that are arranged in a grid, and especially into those arranged inside the grid, the tips have a flange-mounted shoulder from which the pipette tips are suspended in a solid flexurally stiff plate called a magazine. To ensure that all pipette tips are uniformly sealed, only the height of the shoulder on the side of the pipette tips is important, which is a parameter that presents no problem in injection molding technology.

To accelerate the change of the pipette tips, this magazine is not permanently connected to the pipetting device but forms an integral unit with the pipette tips that is detachable from the pipette device.

The magazine loaded with pipette tips is inserted into a suitable holding fixture, hereinafter referred to as magazine holder, in the pipetting device and, to create the seal, is pushed or pulled against the aforementioned sealing plate.

Due to the forces thereby required, all components located in the force transmission path must have a very stable design.

PRIOR ART

WO 02/096562 discloses an automated pipetting system (pipetting device) in which the pipette tips are sealed off from the pipetting channels according to the sealing principle described by means of a pressure plate located between the pipette tips and the pipetting channels.

According to the drawings, in particular Figures in 16 and 17, the pipetting device 500 comprises a pipetting head 600, the lower flat plate 606 (base plate) coming to rest against two lateral blocks 510 after the pipetting head 600 has been inserted into the pipetting device 500. Mounted on the blocks 510 and permanently connected to them is a housing 502 with a cover wall 506 and side walls 508.

The lower flat plate 606 has a gridlike arrangement of through-holes, in this case, for example 8×12, through which the outlet end of a pipetting channel extends.

Attached to the lower flat plate 606 is a sealing plate 672 into which the ends of the pipetting channels extend and which forms the lower outside surface of the pipetting device.

If necessary, the pipetting head 600 can be changed so as to adapt the pipetting device to sample carriers with a different number and configuration of containers in such a way that the pipetting device works with a configuration of pipetting channels identical to the number of containers on the sample carrier.

Next, each end of the pipetting channels that extends through the sealing plate 672 is to be sealingly but detachably connected to each pipette tip 702.

As already explained in the general description of the prior art, the tips 702 have a shoulder 704 from which they are suspended in a magazine 700 in a gridlike arrangement identical to the grid of the pipetting channels.

The magazine holders provided on the side walls 508 are two brackets 530, each comprising a bottom part 534, a side part 532, and a ledge 544.

The two bottom parts 534 serve as a bearing surface for the magazine 700 and thus as a magazine holder.

Extending from both ledges 544 are tension springs 540 with their opposite ends suspended from the side walls 508 via spacer posts 542. The elastic force of the tension springs 540 has the effect that the pipette tips 702 that are located in the magazine 700 are pressed with their shoulder onto the sealing plate 672. The force acting upon the sealing plate 672 is limited by a stop arranged on the mounting support 574 and resting against the lower surfaces of the blocks 510.

In the context of the invention, the brackets 530, in association with the tension springs 540 that are attached via splints 542 to the side walls 508, form the magazine grip.

The above description of an automated pipetting system according to WO 02/096562 is limited to components that are affected by the force transmission path when a loaded magazine 700 is pressed indirectly via the shoulders of the pipette tips 702 and the sealing plate 672 against the lower flat plate.

To ensure a highly defined contact pressure that is determined by the tension springs 540, all components involved in the force transmission path must have a flexurally rigid design at least in the direction of the force transmission path. This requires in particular that the two side walls 508 and the two brackets 530 be made of a solid and consequently heavy material.

Furthermore, for certain applications, it may be a disadvantage if, as in the pipetting device described above, the magazine grip is driven by the same motor that also drives the pump system. In the course of the pipetting cycle, the stroke movement of the upper plate 514 that is responsible for the stroke of the pistons is transferred within a small predetermined stroke range of the plate 514 to the two brackets 530. To this end, spacer pegs 546 that are permanently connected to the brackets 530 extend through oblong holes in the lateral walls into the inside of the housing 502.

In a certain position of the downward stroke movement, the upper plate 514 comes to rest on the free ends of the spacer pegs 546, entrains with it these pegs and thus the brackets 530, on the lower walls 534 of which the magazine rests, interrupting the indirect frictional contact between the magazine 700 and the lower plate 606. The disadvantage is that interrupting the frictional contact requires an even greater force that counteracts the elastic forces.

In summary, the disadvantages of the solution described are, first, that the walls of the housing must necessarily be made of a solid material since the force transmission path extends across the entire height of the housing.

Secondly, the use of tension springs for generating force requires that an even higher counteracting force be generated in order to interrupt the frictional contact for the purpose of changing the magazines.

OBJECTS OF THE INVENTION

Thus, the problem to be solved by the present invention is to make available the most lightweight possible, and thus readily manageable, pipetting device that can be flexibly used as a laboratory apparatus module.

This problem is solved by a pipetting device with the features set forth in the annexed claims.

DESCRIPTION OF THE DRAWINGS

As can be seen.

DESCRIPTION OF THE EMBODIMENTS

Figure 1:
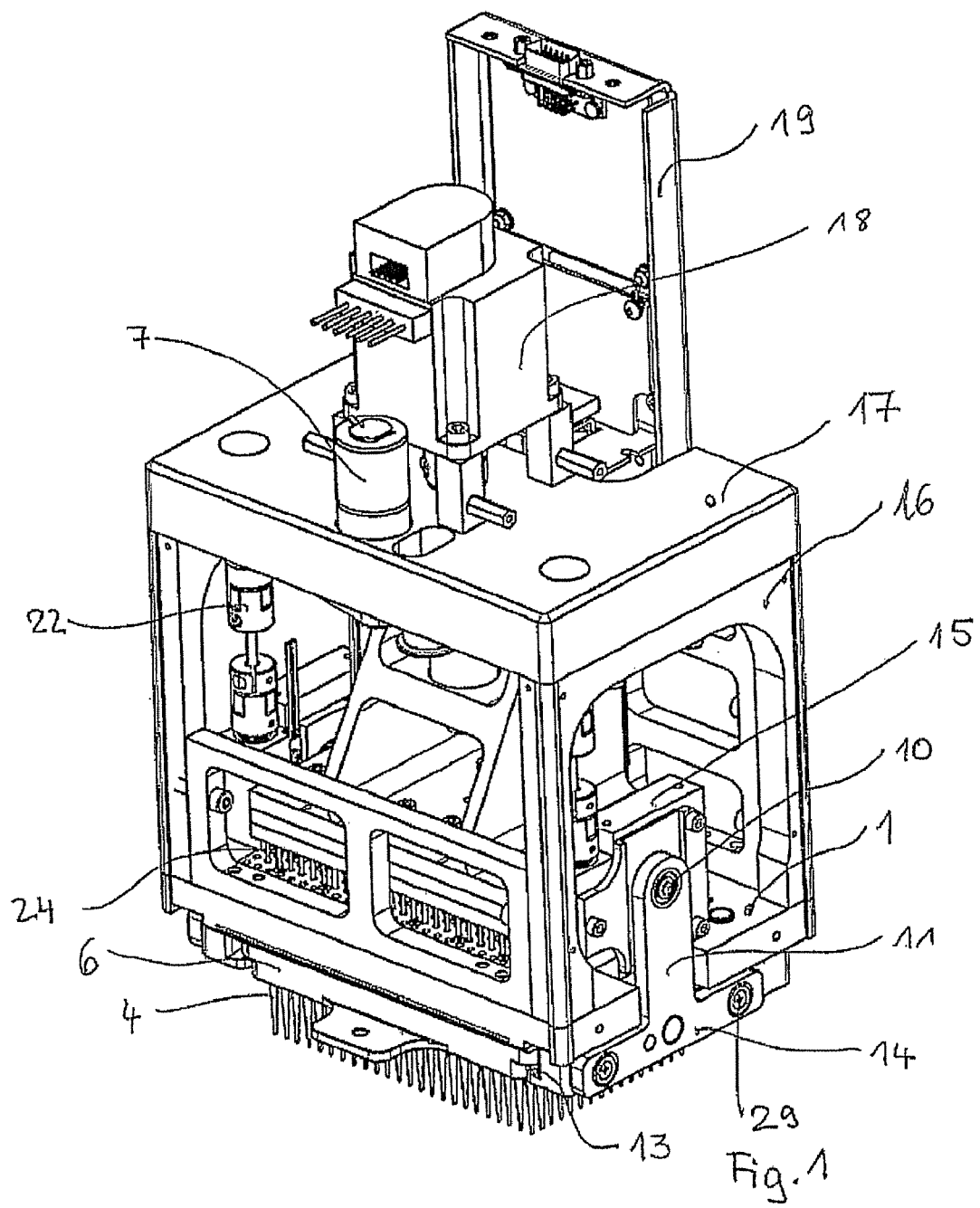
FIG. 1 is a perspective view of the device from above.
Figure 2:
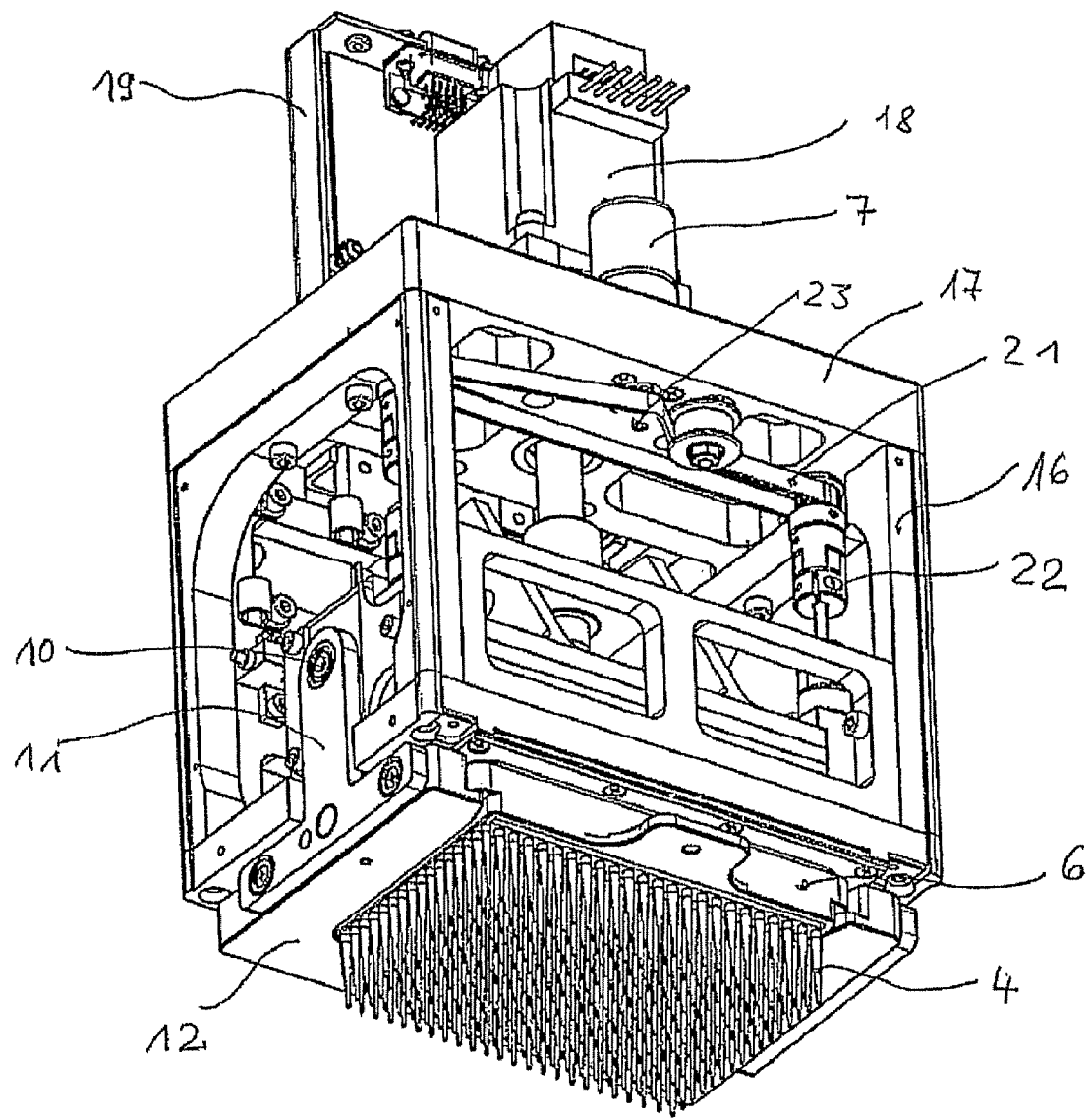
FIG. 2 is a perspective view of the device of FIG. 1 from below.

FIGS. 1 and 2 show an advantageous embodiment of a pipetting device according to the present invention in two different perspective views with an open housing.

The housing of the pipetting device comprises a rectangular housing frame 16 on which is mounted a weight-bearing cover plate 17, on the outside of which a stepper motor 18 for the pump system and a drive motor 7 for the magazine grip of the pipetting device are mounted, a wall 19 attached to the top of the housing, to which wall a housing cap (not shown) is attached so as to be able to cover the two motors 7 and 18, and four lateral cover plates (also not shown in the figure) that are mounted on the housing frame 16 so as to be able to close the side of the housing.

The four lateral cover plates preferably have thin and thus very lightweight walls since these plates serve only to protect the inside of the pipetting device against contamination and are not under any mechanical load.

At the bottom, the housing is closed by a base plate 1. In the base plate 1, a plurality of through-holes are arranged in a predetermined grid (here 16×24) through which the pistons 24 of the pipetting channels 3 of the pump system extend. The pump system is a standard piston stroke system for a pipetting device. The pipetting channels 3 are primarily formed by a guide means 20 and a sleeve 25, which are fitted into each through-hole of the base plate 1, as well as a piston 24 that moves inside these two components, see FIG. 3.

Attached to the base plate 1 on the outside of and resting flat against the housing is a sealing plate 2, which has through-holes in a grid configuration identical to that of the base plate 1, through which the sleeves 25 extend.

Located underneath the base plate 1 is a magazine frame 12 that can move relative to the base plate 1, into which magazine frame a magazine 6 loaded with pipette tips 4 is inserted and vertically pitched with respect to the base plate 1. The magazine frame 12 has a U-shaped design, with a preferably continuous bearing surface 13.

An important feature is that the base plate 1 serves as a contact pressure plate, on the one hand, and as a support for an eccentric drive 9 which transmits the contact pressure, on the other hand. In this manner the stability and flexural rigidity required for the two mechanical functions is ensured by one and the same component.

The outside surfaces of the magazine 6 with tolerance on three sides ensure a defined position of the magazine 6 in the U-shaped magazine frame 12 and thus a defined position of the pipette tips 4 relative to the pipetting channels 3.

The magazine 6 and the base plate 1 are completely flat and flexurally stiff plates so that the pipette tips 4, with their shoulders 5, are uniformly pressed onto the sealing plate 2, with each tip enclosing a pipetting channel 3. The vertically acting contact pressure is distributed in the elastic sealing plate 2 and leads to a force-locking press fit of the ends of the pipetting channels 3, which are formed by the sleeves 25, in the sealing plate 2. This sealing principle in effect between the pipette tips 4 and the pipetting channels 3 is virtually the same as the sealing principle known from the prior art.

The magazine grip is novel. As it is defined here, the magazine grip comprises all components required to pull or push a magazine 6 onto the base plate 1, which produces a hermetically sealed connection between the pipette tips 4 and the pipetting channels 3.

The special feature of the magazine grip is, in particular, that the rotary movement generated by a drive motor 7 is translated via two identical eccentric drives 9 into a stroke movement of the magazine frame 12. The eccentric drives 9 are permanently fixedly mounted on the base plate 1, with the result that the housing of the pipetting device remains completely unaffected by the force transmission path during the pulling of the magazine 6.

In the embodiment example shown in the drawings, the magazine grip comprises primarily the drive motor 7 which is mounted on the cover plate 17, a toothed belt drive 21, shaft couplings 22, two identical stepdown gear units, here in the form of worm gear units 15, and two identical eccentric drives 9, each with an eccentric shaft 8 and a T-shaped gravitational pendulum 11, the cross members 14 of which are connected to the legs of the magazine frame 12.

Figure 4:
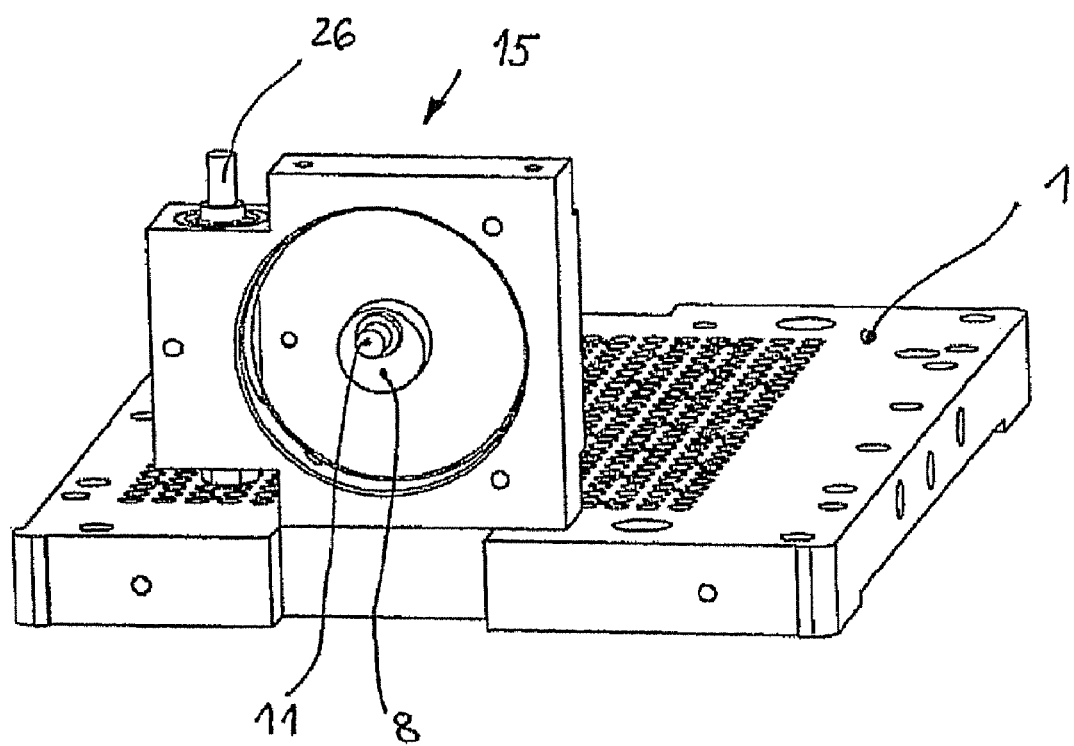
FIG. 4 shows a worm gear mounted on the base plate.

A drive pinion 23 on the pinion shaft of the drive motor 7 drives the toothed belt drive 21 and thus the drive shafts of two shaft couplings 22. The two shaft couplings 22 are arranged vertically opposite each other outside the pump system and, to allow for axial compensation, transmit the rotary movement of the motor via a different shaft coupling 22 to a drive shaft 26 of a worm gear 15, see FIG. 4.

Figure 3:
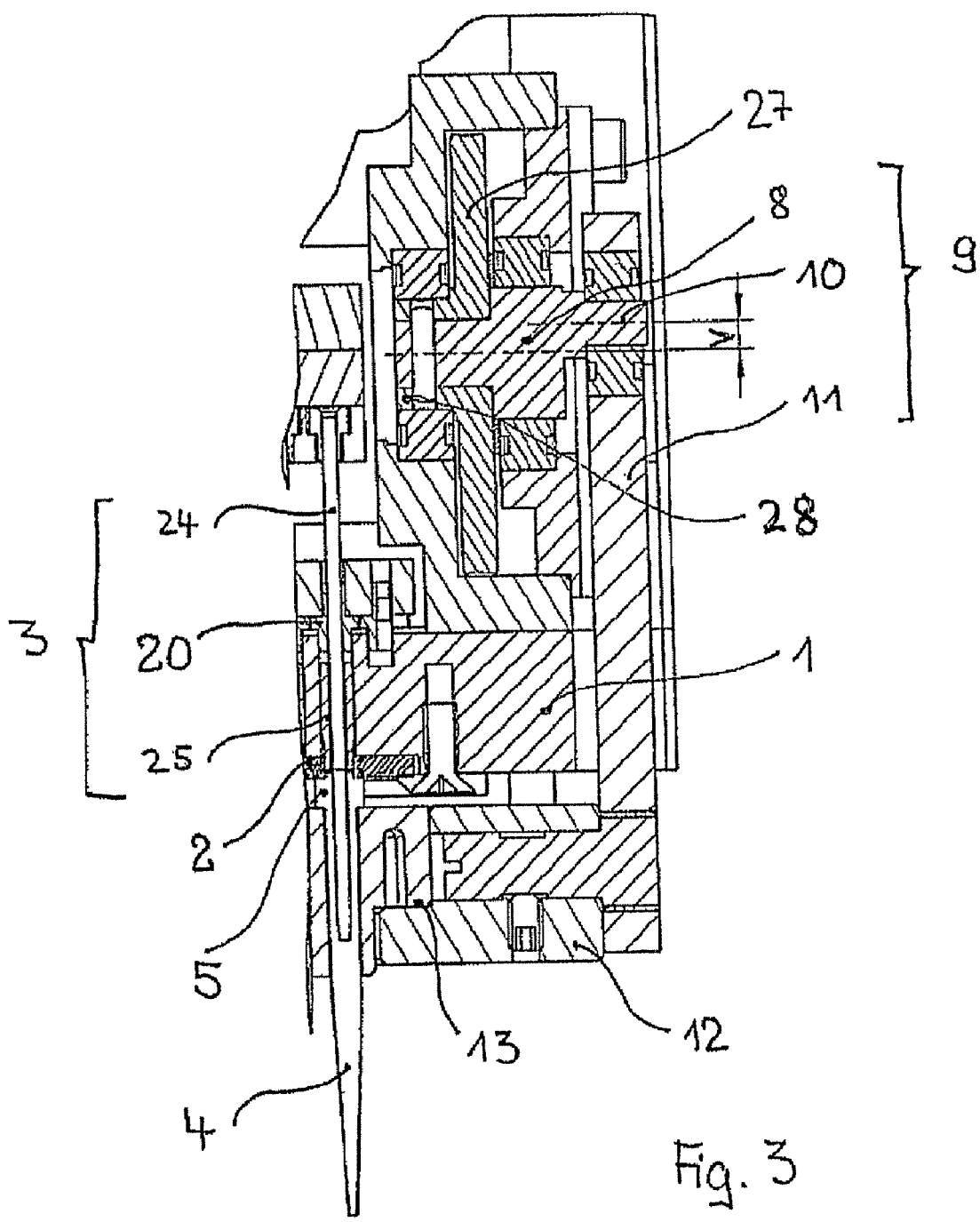
FIG. 3 is a transverse section through a detail of the device of FIG. 1.

The drive shafts of the worm gear units 15 are formed by hollow shafts 28 that are arranged on the worm wheel 27, see FIG. 3.

In each hollow shaft 28, an end of an eccentric shaft 8 is arranged and thus rotates about the axis of a worm wheel 27. On the other ends of the eccentric shafts 8, one eccentric pin 10 each is arranged so as to be staggered by a distance v with respect to the axis of a worm wheel 27, from which eccentric pins one T-shaped gravitational pendulum 11 each is suspended.

During the rotary motor movement of the eccentric shaft 8, the gravitational pendulum 11, and thus the magazine frame 12, performs a wobbling movement, with only the portion of the stroke of the wobbling movement being of functional importance in order to lift and lower the magazine 6 between two possible endpoint positions. In the lowered endpoint position, the magazine 6 can be changed. In the lifted endpoint position, the magazine 6 is pressed with the maximum contact pressure via the shoulders 5 of the pipette tips 4 onto the sealing plate 2.

The offset distance v determines the stroke range and thus also the generated contact pressure.

It is possible to precisely adjust the contact pressure by using small rotatable eccentric studs 29 to create the connection between the cross member 14 of the gravitational pendulum 11 and the legs of the magazine frame 12.

It is therefore important to use an eccentric drive 9 for the magazine grip since only a small vertical range of motion (stroke range) is required, whereas at the end of the range of motion high contact pressures are required.

Because of its high gear reduction, the use of a worm gear 15 as a stepdown gear upstream of the eccentric drive 9 is especially recommended. Furthermore, since the worm gear locks automatically, no other means for maintaining the contact pressure are required.

The input torque of the drive motor 7, which, due to the high gear reduction of the worm gear 15, can be very low, makes it possible for the power transmission components, such as, the toothed belt drive 21 and the shaft couplings 22, to be very small and lightweight, which further contributes to the size and weight reduction.

With the magazine grip described, the force transmission path during the sealing of the pipette tips 4 proceeds directly and over the shortest route from the base plate 1 via the eccentric drive 9 with the gravitational pendulums 11, the magazine frame 12, the magazine 6 and the shoulders 5 to the sealing plate 2, so that only a small number of components of the pipetting device are affected by the mechanical load generated.

Compared with devices of the same generic type, the pipetting device can have a smaller and more lightweight design and can therefore be more flexibly used as a module in laboratory operations. This means that the pipetting device can be permanently or movably mounted in order to perform a necessary relative movement between the pipette tips 4 and a container for aspirating and dispensing liquids.

| List of reference characters | |
|---|---|
| 1 | Base plate |
| 2 | Sealing plate |
| 3 | Pipetting channels |
| 4 | Pipette tip |
| 5 | Shoulder |
| 6 | Magazine |
| 7 | Drive motor |
| 8 | Eccentric shaft |
| 9 | Eccentric drive |
| 10 | Eccentric pin |
| 11 | Gravitational pendulum |
| 12 | Magazine frame |
| 13 | Bearing surface |
| 14 | Cross member of a gravitational pendulum |
| 15 | Worm gear |
| 16 | Housing frame |
| 17 | Cover plate |
| 18 | Stepper motor |
| 19 | Wall attached to the top of the housing |
| 20 | Guide means |
| 21 | Toothed belt drive |
| 22 | Shaft coupling |
| 23 | Drive pinion |
| 24 | Piston |
| 25 | Sleeve |
| 26 | Drive shaft of the worm gear |
| 27 | Worm wheel |
| 28 | Hollow shaft |
| 29 | Eccentric stud |
| v | Offset |

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A pipetting device, comprising a base plate, an elastic sealing plate that covers the outside of the base plate, a plurality of pipetting channels arranged in a predetermined grid extending through the base plate and the sealing plate, a magazine loaded in the same grid with pipette tips, each pipette tip having a shoulder, said magazine arranged in a magazine holder indirectly frictionally connected via the shoulders and the sealing plate with the base plate, and a drive motor, indirectly connected to the eccentric shafts of two identical eccentric drives that are permanently mounted on the support on the base plate and each of which having an eccentric pin that is offset by a distance with respect to the axis of the eccentric shaft, one T-shaped gravitational pendulum being suspended from each of said eccentric pins, said magazine holder being formed by a U-shaped magazine frame with a bearing surface on the inside and the magazine frame, on its lateral legs, is connected to the cross member of each gravitational pendulum so as to be able to lift and lower the magazine frame relative to the base plate.

2. The pipetting device of claim 1, further comprising an additional identical stepdown gear arranged in the connection between the drive motor and the eccentric shafts of the eccentric drives.

3. The pipetting device of claim 2, wherein the stepdown gear units are worm gears.

4. The pipetting device of claim 3, wherein the worm wheels of the worm gear units form the eccentric disks of the eccentric drives.

5. The pipetting device of claim 1, wherein the connection between the cross member of the gravitational pendulum and the legs of the magazine frame is formed by small rotatable eccentric studs.

* * * * *